(12) United States Patent
Yao et al.

(10) Patent No.: US 8,455,620 B2
(45) Date of Patent: Jun. 4, 2013

US008455620B2

(54) CLONING AND EXPRESSION OF A NOVEL PHYTASE

(75) Inventors: Bin Yao, Beijing (CN); Huiying Luo, Beijing (CN); Huoqing Huang, Beijing (CN); Yaru Wang, Beijing (CN); Tiezheng Yuan, Beijing (CN); Xiuyun Shi, Beijing (CN); Yingguo Bai, Beijing (CN); Kun Meng, Beijing (CN); Peilong Yang, Beijing (CN)

(73) Assignee: Feed Research Institute Chinese Academy of Agricultural Sciences, Beijing (CN)

( * ) Notice: Subject to any disclaimer, the term of this patent is extended or adjusted under 35 U.S.C. 154(b) by 1116 days.

(21) Appl. No.: 12/298,948

(22) PCT Filed: Apr. 30, 2006

(86) PCT No.: PCT/CN2006/000893
§ 371 (c)(1),
(2), (4) Date: Oct. 29, 2008

(87) PCT Pub. No.: WO2007/128160
PCT Pub. Date: Nov. 15, 2007

(65) Prior Publication Data
US 2010/0092613 A1 Apr. 15, 2010

(51) Int. Cl.
*C07K 14/195* (2006.01)
(52) U.S. Cl.
CPC ............ *C07K 14/195* (2013.01); *Y10S 530/825* (2013.01)
USPC .......................................... 530/350; 530/825

(58) Field of Classification Search
None
See application file for complete search history.

(56) References Cited

U.S. PATENT DOCUMENTS
2003/0101476 A1 * 5/2003 Short et al. .................... 800/278

FOREIGN PATENT DOCUMENTS
| CN | 1231692 | 10/1999 |
| CN | 1277207 | 12/2000 |
| CN | 1451039 | 10/2003 |
| CN | 1602357 | 3/2005 |
| WO | 0248332 | 6/2002 |

* cited by examiner

*Primary Examiner* — Anish Gupta
(74) *Attorney, Agent, or Firm* — Lowe Graham Jones PLLC (57) ABSTRACT

The present invention relates to a novel phytase enzyme, a novel isolated nucleic acid molecule coding the enzyme, and a novel *Yersinia intermedia* having phytase activity. Particularly, the present invention relates to the phytase having (a) Theoretical molecular weight 45.5 kDa, (b) high specific activity 3960±248 U/mg, (c) high stability at high temperature and wide pH, (d) optimal pH of 4.0-5.0, (e) optimal temperature of 50-60° C., (f) high resistance to pepsin and trypsin. The phytase is very suitable to be used in feed of monogastrics as feed additive. The present invention also relates to a recombinant vector comprising said nucleic acid molecule, a recombinant host cell (e.g., *Pichia pastoris*) harboring said recombinant vector, and a method for producing phytase using the recombinant host cell. The present invention further provides a feed additive comprising said phytase and/or host cells expressing a phytase as effective ingredient. In addition, the present invention provides a novel method for isolating phytase from a target organism.

3 Claims, 4 Drawing Sheets

CLONING AND EXPRESSION OF A NOVEL PHYTASE

REFERENCE TO RELATED APPLICATIONS

This application is a 35 U.S.C. §371 filing of PCT/CN2006/000893 filed on Apr. 30, 2006 and which is incorporated by reference herein in its entirety.

FIELD OF THE INVENTION

The present invention relates to a novel phytase gene, a phytase enzyme encoded by the gene, a *Yersinia intermedia* strain producing the enzyme, a method for expressing the enzyme in a host cell such as *Pichia Pastoris*, and a feed additive containing the protein as an effective ingredient. Furthermore, the present invention provides an easy and rapid method for isolating of phytase gene from a target organism.

BACKGROUND OF THE INVENTION

Phytic acid takes up about 50-70% of phosphate contained in animal forages. However, monogastric animals such as fowls and pigs lack digestive enzymes for separating inorganic phosphorus from the phytic acid molecule, so that a coefficient of utilization of phosphorus is very low. Phosphate of phytic acid is not absorbed, passes through the digestive tract and is excreted. This leads to an increased ecological phosphorus burden to land and water. In addition, since phytate chelates several essential minerals and prevents or inhibits their absorption in the digestive tract, phytic acid decreases the nutritional value of food and animal feeds.

Obviously, phosphorous (P) is an essential element for growth, so that inorganic phosphorus (e.g., dicalcium phosphate, defluorinated phosphate) or animal products (e.g., meat and bone meal, fish meal) are added to meet the animals' nutritional requirements for phosphorus, and it is very expensive.

Phytases, a specific group of monoester phosphatases, are required to initiate the release of phosphate ("P") from phytic acid (myo-inositol hexophosphate), the major storage form of P in cereal foods or feeds (E Graf et al. 1987). Phytase is widely distributed in plants, animals and microorganisms. Based on the characteristics of phytases from different organisms, microbial phytase are getting more and more attention. And, microbial phytase, as a feed additive, has been found to improve the bioavailability of phytate phosphorous in typical monogastric diets (Cromwell, et al, 1993). The result is a decreased need to add inorganic phosphorous to animal feeds, as well as lower phosphorous levels in the excreted manure (Kornegay, et al, 1996). With the development of gene engineering, on the one hand, more and more microbial phytases have been isolated and/or purified. For example, "Purification and Characterization of a Phytase from *Klebsiella terrigena*," (Greiner et al. 1997), "Purification and Properties of a Thermostable Phytase from *Bacillus* sp. DS11," (Kim et al. 1998), "Isolation and characterization of a phytase with improved properties from *Citrobacter braakii*" (Kim et al 2003), and "Gene cloning, expression and characterization of novel phytase from *Obesumbacterium proteus*" (Zinin et al 2004); on the other hand, improved properties of the conventional phytase have been achieved by Site-directed mutagenesis or gene shuffling. For example, Improving thermostability of *Aspergillus niger* phytase by elongation mutation (chen et al, 2005), or Site-directed mutagenesis of *Escherichia coil* phytase (Lei X G, 2005). So manufacture costs of microbial phytase was reduced largely. Because of these advantages, some of the known phytases have gained widespread acceptance in the feed industry.

However, problems still exist in these known phytases. Because these phytases do not react ideally as an additive in feed, most phytases have completely lost their activity during feed pelleting process and are unable to degrade phytic acid in stomach or intestines. The reasons for this vary from enzyme to enzyme. Typical concerns relate to poor stability and low activity of the enzyme in the environment of the desired application. For example, the temperature encountered in the processing of feedstuffs, the pH and the proteases in the digestive tracts of animals, and the degradation during storage.

It is, thus, generally desirable to discover and develop novel enzymes having good stability and phytase activity for use in connection with animal feed, and to apply advancements in fermentation technology to the production of such enzymes in order to make them commercially viable.

On the other hand, conventional methods to obtain a new phytase gene are mainly based on screen form genomic library or direct separation of proteins. However, the conventional methods were very laborious, difficult and expensive. And it is well known that phytases are of relatively low homology among different species, which present a challenge for traditional approach to isolate a phytase gene.

SUMMARY OF THE INVENTION

With the aim to solve the problem existing in the art, we have isolated a novel microorganism producing phytase from thousand of strains from the frozen soil from the China No. 1 glacier (Xinjiang province). We have also identified the nucleotide sequence, which encodes the protein having phytase activity. The phytase reached a relatively high level expression in host cells such as *Pichia pastoris*. Consequently, the recombinant *Pichia* expression system is suitable for industrial production. And the novel phytase has several excellent characteristics, which are more conformable to improve feed efficiency.

Thus, in one aspect, the present invention provides a brand new *Yersinia intermedia* strain producing phytase.

The present invention also provides a novel gene coding a protein with phytase activity, which nucleotide acid sequence is a nucleic acid molecule depicted in SEQ ID NO: 2 or a derivate thereof.

Yet another aspect of the invention is a phytase having the following characteristics: a) Molecular weight of 46 kDa; b) Optimal pH of 4.0-5.0; c) Optimal temperature of 50-60° C.; d) Theoretical pI value of 7.7; e) High specific activity over 3000 U/mg; and f) High resistance to pepsin and trypsin. Such a phytase can be from a microorganism belonging to the Genus of *Yersinia*, preferably *Yersinia intermedia*.

Therefore, the present invention relates to an isolated protein that is selected from:

a) a polypeptide comprising the amino acid as shown in SEQ ID NO. 3;
b) a polypeptide with phytase activity which is encoded by a polynucleotide of SEQ ID NO: 2 or a polynucleotide sequence that is degenerated as a result of the genetic code to SEQ ID NO: 2;
c) a polypeptide with phytase activity which is encoded by a polynucleotide that hybridizes under stringency conditions with the complementary chain of a polynucleotide as shown in SEQ ID NO: 2;

d) a polypeptide with phytase activity which is encoded by an allele or natural variant of the polynucleotide as shown in SEQ ID NO: 2;

e) a polypeptide with phytase activity which is derived from SEQ ID NO: 3 by substitution, deletion and/or insertion of one or more amino acid residues; or f) a polypeptide with phytase activity and having at least 60% homology with the amino acid as set forth in SEQ ID NO: 2, preferably at least 65%, 70%, 75%, 80%, 85%, or at least 90%, particularly at least 95%

The present invention further provides an easy and efficacious method obtaining a phytase enzyme gene from genome DNA, comprising:

a) designing a pair of degenerate primers based on the conserved sequences of phytase, i.e., THGXRXP (SEQ ID NO: 6) and HD;

b) PCR amplifying partial sequence of phytase using said primers; and c) obtaining the whole sequence of phytase through TAIL-PCR.

In another aspect, the present invention provides a recombinant vector comprising said nucleic acid encoding phytase, a recombinant host cell (such as *Pichia Pastoris*) having been introduced said vector or said nucleic acid molecule, as well as a method for expressing the enzyme in a host cell.

The present invention further relates to the use of said phytase or a phytase-producing host cell in preparation of a feed additive, as well as the feed additive containing the protein and/or host cell as an effective ingredient. The feed additive of the present invention can be effectivity used for the production of animal feeds since it contained phytase, which enhance the hydrolyzation of phytic acid.

DEPOSITION ABOUT THE BIOLOGICAL MATERIAL

The novel "*Yersinia intermedia* H-27" isolated by the inventors has been deposited under Budapest Treaty at China General Microbiological Collection Center, Beijing, China (CGMCC), located at the Institute of Microbiology Chinese Academy of Sciences, NO. 1 Beichen West Road, Chaoyang District, Beijing 100101, China, on Apr. 25, 2006, with the Accession Number of CGMCC 1702.

DESCRIPTION ABOUT THE SEQUENCES

SEQ ID NO: 1, 16S rDNA of *Yersinia intermedia* H-27;

SEQ ID NO: 2, polynucleotide sequence encoding the novel phytase;

SEQ ID NO: 3, amino acid sequence of the novel phytase;

SEQ ID NO: 4, Forward degenerate primer for cloning of phytase;

SEQ ID NO: 5, Reverse degenerate primer for cloning of phytase.

DETAIL DESCRIPTION OF THE INVENTION

In order to achieve the above object, firstly, the present invention provides a strain having phytase activity. The strain having phytase activity was separated from samples of frozen soil from the China No. 1 glacier (Xinjiang province). Activity of phytase produced in the strain was measured by ferrous sulfate-molybdenum blue method. And the strain showing phytase activity was identified by using 16s rRNA sequence analysis. As a result, the base sequence of 16S rDNA showed 99.5% homology with that of *Yersinia intermedia* and 99% homology with sequences of *Yersinia aldovae* and *Yersinia mollaretii*, so the strain of the present invention was confirmed to be a novel strain.

The strain was a Gram-negative, rob-type bacterium having a similarity to *Escherichia coli* in size, which was observe under light microscope. From the investigation of the biochemical and physiological characteristics, the strain was confirmed to be a facultative aerobic microorganism, meaning that it could be growing with or without oxygen. And the optimum temperature for growth of the strain was 30° C.

Based on the results of investigation on morphological, physiological and 16s rDNA of the strain, and the strain separated in the present invention was named as "*Yersinia intermedia* H-27" and deposited at China General Microbiological Collection Center (CGMCC), on Apr. 25, 2006, with the Accession Number of CGMCC 1702.

The present invention relates to a phytase with the following characteristics: a) Molecular weight of 46 kDa; b) Optimal pH of 4.0-5.0, preferably 4.5; c) Optimal temperature of 50-60° C., preferably 55° C.; d) Theoretical pI of 7.7; e) High specific activity over 3000 U/mg, preferably over 3300 U/mg, e.g., 3400, 3500, 3600, 3700, 3800, 3900, 4000, 4100, 4200, 4300, 4400, or 4500 U/mg; and f) High resistance to pepsin and trypsin. Such a phytase can be derived from a microorganism belonging to the Genus of *Yersinia*, preferably *Yersinia intermedia*.

The present invention also provides to an isolated protein comprising the amino acid sequence depicted in SEQ ID NO: 3. Preferably, said enzyme is encoded by a polynucleotide of SEQ ID NO: 2 or a polynucleotide sequence that is degenerated as a result of the genetic code to SEQ ID NO: 2. In another embodiment, the present invention relates to a derivate of said protein, which is obtainable from SEQ ID NO: 3 by substitution, deletion and/or insertion of one or more (e.g., one or several, or a value selected from 1-10, e.g., 1, 2, 3, 4, 5, 6, 7, 8, 9 or 10, or ranges intermediated to the above-recited values) amino acid residues. For example, a common strategy is conservative amino acid substitutions that is to say the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, replacement with another amino acid residue from the same side chain of one or more amino acid residue would not substantially change the enzyme activity of said phytase. Furthermore, it is well known in the art that during the cloning of genes, usually enzyme recognition sites are designed, which would result in one or several non-relating amino acid residues on the ends of target protein without affecting the activity thereof. In addition, in order to construct a fusion protein, to enhance expression of recombinant protein, to obtain an recombinant protein automatically secreted outside the host cell, or to aid in the purification of the recombinant protein, suitable peptide linker, signal peptide, leader peptide, terminal extensions, glutathione S-transferase (GST), maltose E binding protein, protein A, tags such as 6His or Flag, or proteolytic cleavage site for Factor Xa, thrombin or enterokinase are usually introduced into the N- or C-terminus of the recombinant protein or within other suitable regions in the proteins.

In another embodiment, the protein with phytase activity according to the present invention can comprise an amino acid sequence which is encoded by a nucleotide sequence which hybridizes, e.g., hybridizes under stringent conditions, to a nucleotide sequence of SEQ ID NO: 2 as set forth in the Sequence Listing. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to one of ordinary skill in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. A person skilled in the art understands that high stringent condition could be realized by raising the hybridization temperature up to 50° C., 55° C., 60° C. or 65° C.

Besides, it will be appreciated by one of ordinary skill in the art that genetic polymorphism due to natural variation may exist among individuals within a population. Such natural variations can typically result in 1-5% variance in the nucleotide sequence of the phytase gene. Any and all such nucleotide variations and resulting amino acid polymorphisms in phytase that are the result of natural variation and that do not alter the functional activity of phytase proteins are intended to be within the scope of the invention. Therefore, the present invention also encompasses a polypeptide with phytase activity encoded by such an allele or natural variant of the polynucleotide as shown in SEQ ID NO: 2.

In a preferred embodiment, a phytase protein is such a active protein that is at least about 60%, 61%, 62%, 63%, 64%, 65%, 66%, 67%, 68%, 69%, or at least about 70%, 71%, 72%, 73%, 74%, 75%, 76%, 77%, 78%, 79%, or at least about 80%, 81%, 82%, 83%, 84%, 85%, 86%, 87%, 88%, 89%, or at least about 90%, 91%, 92%, 93%, 94%, 95%, 96%, 97%, 98%, more preferably at least about 98.1%, 98.2%, 98.3%, 98.4%, 98.5%, 98.6%, 98.7%, 98.8%, 98.9%, and even more preferably at least about 99%, 99.1%, 99.2%, 99.3%, 99.4%, 99.5%, 99.6%, 99.7%, 99.8%, 99.9% or more homologous to the entire amino acid sequence as shown in SEQ ID NO: 3 of the present invention. Ranges and identity values intermediated to the above-recited values (e.g., 60-90% homologous or 98.1-99.9% identical) are also intended to be included in the present invention. For example, ranges of identity values using a combination of any of the above values recited as upper and/or lower limits are intended to be included. The comparison of sequences and determination of percent homology between two sequences are art-known techniques, and can be accomplished using a mathematical algorithm, such as commercially available softwares or those integrated in public databases, for example, multi sequence alignment program CLUSTAL W BLOCKS or BLAST, etc. one of ordinary skill in the art will know how to optimize the parameters of the program (e.g., score, word length, weight, gap penalty, and so on) for the specific sequence being analyzed. Using the default set of parameters in BLAST of GenBank, the following alignment results were obtained.

TABLE 1

Alignment results with other known phytase

| Source | Genbank Accession. No. | Homology |
|---|---|---|
| *Obesumbacterium proteus* | AY378096 | 53% |
| *Escherichia coli* | AAN28334 | 45% |

On the other hand, the present invention provides a novel phytase gene of SEQ ID NO: 2. The invention further encompasses nucleic acid molecules that differ from one of the nucleotide sequences depicted in SEQ ID NO: 2 of the invention due to degeneracy of the genetic code and thus encode the same phytase protein. In another embodiment, an isolated nucleic acid molecule of the invention is a nucleotide sequence which hybridizes, e.g., hybridizes under stringent conditions, to a nucleotide sequence of SEQ ID NO: 2, with the allele or natural variant thereof is preferred. In another embodiment, an isolated nucleic acid molecule of the invention has a nucleotide sequence encoding a protein having an amino acid sequence shown in the SEQ ID NO: 3. In a still further embodiment, the nucleic acid molecule of the invention encodes a full length phytase protein which is substantially homologous to an amino acid sequence of SEQ ID NO: 3, for example, a protein that derived from SEQ ID NO: 3 by substitution, deletion and/or insertion of one or more (e.g., one or several, or a value selected from 1-10) amino acid residues, or one that is at least 99% homologous to the amino acid sequence of SEQ ID NO: 3. Such a nucleic acid molecule is preferably at least about 60%, 61%, 62%, 63%, 64%, 65%, 66%, 67%, 68%, 69%, or at least about 70%, 71%, 72%, 73%, 74%, 75%, 76%, 77%, 78%, 79%, or at least about 80%, 81%, 82%, 83%, 84%, 85%, 86%, 87%, 88%, 89%, more preferably at least about 90%, 91%, 92%, 93%, 94%, 95%, 96%, 97%, 97.7%, 97.8%, 97.9%, or at least about 98%, 98.1%, 98.2%, 98.3%, 98.4%, 98.5%, 98.6%, 98.7%, 98.8%, 98.9%, and even more preferably at least about 99%, 99.1%, 99.2%, 99.3%, 99.4%, 99.5%, 99.6%, 99.7%, 99.8%, 99.9% or more homologous to a nucleotide sequence of SEQ ID NO: 2. Ranges and identity values intermediate to the above-recited values (e.g., 76-97% homologous or 97.8-99.9% identical) are also intended to be included in the present invention. Using the default set of parameters in BLAST of GenBank, the following alignment results were obtained.

TABLE 2

Alignment results

| Source/peptide encoded | Genbank Accession. No. | Homology |
|---|---|---|
| *Obesumbacterium proteus*/phytase | AY378096 | 56% |
| *Escherichia coli*/phytase | AF537219 | 50% |

In yet another embodiment, the present invention relates to a recombinant vector comprising said nucleic acid encoding phytase, a recombinant host cell (such as *Pichia Pastoris*) having been introduced said vector or said nucleic acid molecule, as well as a method for expressing the enzyme in a host cell. As used herein, the term "vector" refers to a nucleic acid molecule capable of transporting another nucleic acid to which it has been linked, which can be, for example, a plasmid or a viral vector. The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, repressor binding sites, activator binding sites, enhancers and other expression control elements (e.g., terminators, polyadenylation signals, or other elements of mRNA secondary structure). It will be appreciated by one of ordinary skill in the art that the design of the expression vector can depend on such factors as the choice of the host cell to be transformed, the level of expression of protein desired, etc. The expression vectors of the invention can be introduced into host cells to thereby produce proteins or peptides, including fusion proteins The recombinant expression vectors of the invention can be designed for expression of phytase proteins in prokaryotic or eukaryotic cells. For example, phytase gene can be expressed in bacterial cells such as *E. coli*, yeast such as *Pichia* or *Aspergillus*, insect cells (e.g., Sf9 cell or silkworm cell, using baculovirus expression vectors), or plant cell (such as *Arabidopsis*, tobacco, corn, and so on, mediated by *Agrobacterium tumefaciens*). Thus, the invention pertains to host cells into which a recombinant expression vector of the invention has been introduced, with *Pichia* preferred. *Pichia pastoris* is a methylotrophic yeast, capable of metabolizing methanol as its sole carbon source. This system is well-known for its ability to express high levels of heterologous proteins. As an effective expression system, many of phytase gene have successfully expressed in *P. pastoris*. The novel phytase gene also expressed in *P. pastoris* and had high levels of expression. The extracellular phytase activity is 389 unit/ml after inducing 48 hours in 500 ml flask. So it will be very easy to mass-produce the phytase by fermentation, and the cost will be lower than ever.

Vector DNA can be introduced into prokaryotic or eukaryotic cells via conventional transformation or transfection techniques. As used herein, the terms "transformation" and "transfection", "conjugation" and "transduction" are intended to refer to a variety of art-recognized techniques for introducing foreign nucleic acid (e.g., linear DNA or RNA (e.g., a linearized vector or a gene construct alone without a vector) or nucleic acid in the form of a vector (e.g., a plasmid, phage, phasmid, phagemid, transposon or other DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

A host cell of the invention, such as a prokaryotic or eukaryotic host cell in culture, can be used to produce (i.e., express) a phytase protein. Accordingly, the invention further provides methods for producing phytase proteins using the host cells of the invention. In one embodiment, the method comprises culturing the host cell of invention (into which a recombinant expression vector encoding a phytase protein has been introduced, or into which genome has been introduced a gene encoding a wild-type or altered phytase protein) in a suitable medium until phytase protein is produced. In another embodiment, the method further comprises isolating phytase proteins from the medium or the host cell.

Yet another aspect of the invention is the phytase expressed in *Pichia pastrois*. In order to ascertain the assay of the phytase, the phytase was purified by simple approach, such as ammonium sulfate precipitation, dialysis, ultrafiltration and chromatography. After the simple purification, the purity of the phytase is enough to study the enzyme properties. The phytase purified has a molecular weight of 45 kDa on SDS-PAGE and is activated when using phytic acid as a substrate. The phytase is an acidic enzyme showing a high enzyme activity at 50° C.-60° C. and the optimal activity is observed at 55° C. The enzyme activity is very stable between pH 1.0 and pH 10.0, the best activity can be seen between pH 4.0 and pH 5.0, and the optimal pH is 4.5. The enzyme activity is strongly inhibited by $Fe^{2+}$, $Zn^{2+}$ and $Cu^{2+}$, and was not significantly changed with other metal ions. And the enzyme has a high stability at higher temperatures, when the enzyme was left at 80° C. for 1 hour, 40% of the activity was remained. Besides, the phytase shows a strong resistance against trypsin and pepsin.

Further, the present invention further relates to the use of said phytase or a phytase-producing host cell in preparation of a feed additive, as well as the feed additive containing the protein and/or host cell as an effective ingredient. The feed additive of the present invention can be effectively used for the production of animal feeds since it contained phytase, which enhancing utilization of phosphorus in feeding grains.

The feed additive of the present invention can be prepared in the form of dried or liquid formulation, and can additionally include one or more enzyme preparations. The additional enzyme preparation can also be in the form of dried or liquid formulation and can be selected from a group consisting of keratinase, lipolytic enzymes like lipase, and glucose-producing enzymes such as amylase hydrolyzing a-1,4-glycoside bond of starch and glycogen, phosphatase hydrolyzing organic phosphate, carboxymethylcellulase decomposing cellulose, xylanase decomposing xylose, maltase hydrolyzing maltose into two glucoses and invertase hydrolyzing saccharose into glucose-fructose mixture.

The feed additive of the present invention can additionally include other non-pathogenic microorganisms, in addition to phytase or a microorganim producing phytase. The additional microorganism can be selected from a group consisting of *Bacillus subtilis* that can produce protease, lipase and invertase, probiotics such as *Bifidobacterium*, *Lactobacillus* sp.

strain having an ability to decompose organic compounds and physiological activity under anaerobic conditions, filamentous fungi like *Aspergillus oryzae* that increases the weight of domestic animals, enhances milk production and helps digestion and absorptiveness of feeds, and yeast like *Saccharomyces cerevisiae*.

The present invention further provides an easy and efficacious method obtaining a phytase gene from genome DNA. There were two conventional methods to obtain a new phytase gene, one way was that a new phytase gene was isolated from genomic library, the other was started with protein. However, the conventional methods were very laborious, difficult and expensive. In order to solve the above-mentioned problem, we tried to develop a method that can easily obtain a phytase gene by combing a various known technologies. By analyzing a large number of amino acid sequences of histidine acid phosphatase, a mainly kind of phytase, we found that there were two conserved sequences, RHGXRXP (SEQ ID NO: 7) and HD in histidine acid phosphatase, by the BLOCKS [http://blocks.fhcrc.org/blocks/make_blocks.html], Based on the two conserved sequences and the bias codons in different organism, we designed a degenerate primer, namely, Forward degenerate primer, FI, 5'-GTKSTKAWWKTSAGYCGCCA-3' (20mer) (SEQ ID NO: 4), and Reverse degenerate primer, RI, 5'-TWKGC-MAKRTTRGTATCRTG-3' (20mer) (SEQ ID NO: 5), which was used to amplify a part of sequence of phytase gene from chromosomal DNA by PCR (wherein the meanings of each abbreviation shown in Table 3 below). The part of sequence in all known histidine acid phosphatase is about 900 bp, and according to the size of the part of sequence, we could screen the PCR product by electrophoresis on agarose gel. And then the approximate 900 bp DNA was sequenced and analyzed by BLAST program. According to results analyzed by BLAST program, we could make a conclusion: whether or not the approx 900 bp sequence was a novel phytase gene.

If the result of analysis shows that the approx 900 bp sequence is a part of novel phytase gene. The next step is to obtain the whole sequence of the novel phytase gene. In order to obtain the whole sequence of the probable phytase gene, the upstream and downstream regions of the part of sequence were cloned respectively by TAIL-PCR (Liu et al., 1995).

Compared with the conventional methods, the novel method is very convenient, effective, inexpensive and simple to obtain a novel phytase gene. We had obtained two novel phytase genes by this method (one from *Yersinia intermedia* H-27 described in this application and the other from *Citrobacter amalonaticus* described in another application of the inventors).

TABLE 3

| Abbreviation to represent ambiguity | |
|---|---|
| M = A or C | V = A or C or G |
| R = A or G | H = A or C or T |
| W = A or T | D = A or G or T |
| S = C or G | B = C or G or T |
| Y = C or T | N = A or C or G or T |
| K = G or T | |

EXAMPLES

The present invention is further illustrated with reference to the following Examples and the appended drawings, which should by no means be construed as limitations of the present invention.

Example 1

Separation Phytase-Producing Strain

Phytase-producing strain was separated from samples of frozen soil from the China No. 1 glacier (Xinjiang province). Particularly, in order to find a phytase-producing strain, Samples of frozen soil from the China No. 1 glacier (Xinjiang province) were collected in April 2005 and stored for several days in an ice chest until they could be processed in the laboratory. The frozen soil was suspended in sterile water and diluted. Then, the supernatant of different samples were inoculated into LB medium without agar, followed by respective cultivation at 4° C., 10° C., 15° C. and 30° C. for 1-2 days. Phytase activities in the culture solution and in cell disruption solution, of different samples at different culture temperatures, were measured by ferrous sulfate-molybdenum blue method (as detailed below in Example 4). Phytase activities were measurable in cell disruption solution, which showed that those strains had intracellular phytase activity. Samples with phytase activities were primarily selected and the appropriate culture temperature was determined to be 30° C. The Samples with phytase activities were diluted and smeared on LB medium with 1.5% agar by cultivation in a 30° C. incubator for 1 day. Different colonies with various morphologies were selected, inoculated into 5 ml LB medium, and then incubated over night. Phytase activity of each colony in cell disruption solution was measured and one out of the selected colonies, which showed the highest phytase activity, was selected finally. The strain with phytase activity was numbered as H-27.

Example 2

Analysis of Characteristics of H-27 Strain Producing a Phytase

The H-27 strain isolated in the above Example 1, was confirmed to be a gram negative bacterium through Gram straining. The strain was a rod type bacterium, having a similar size to *Escherichia coli* under light microscope. Some of the biochemical and physiological characteristics of the strain were further investigated. As a result, the strain was a gram negative, facultative aerobic microorganism that could growing with or without oxygen, and the optimum temperature for growth was found to be 30° C. We also analyzed 16s rRNA sequence of the strain. The 16s rDNA sequence (SEQ ID NO: 1) of the strain was amplified by PCR using the Promega Taq kit, and the 16S rDNA sequence of this strain was aligned with reference sequences from GenBank by using BLAST and the multiple sequence alignment program CLUSTAL W. As a result, the base sequence of 16S rDNA showed 99.5% homology with that of *Yersinia intermedia* and 99% homology with the sequence *Yersinia aldovae* and *Yersinia mollaretii*.

Based on the results of investigation on morphological, physiological and 16s rDNA of the selected strain, we could identify the strain as a novel *Yersinia intermedia*.

According to the above result and the record number used during research, this strain was designated as "*Yersinia intermedia* H-27" and was deposited at China General Microbiological CC Center (CGMCC), on Apr. 25, 2006 (Accession No.: CGMCC 1702).

Example 3

Cloning of Phytase Gene

Homology-based cloning may be effective and convenient when the protein whose gene to be cloned is a known member of a multi-gene family. Often, amino acid sequence and DNA sequence alignment of family members reveal a particularly conserved sequence.

Obviously, according to the classification of phytases, most phtyases from bacteria belong to the family of histidine acid phosphatase (HAP). Upon analysis of various sequences from HAP family by the multiple sequence alignment program CLUSTAL W and the BLOCKS (http://blocks.fhcrc.org/blocks/make_blocks.html), we found that there were two conserved sequences among HAP enzymes, namely, RHGXRXP (SEQ ID NO: 7) and HD. Starting from said two conserved sequences, it was possible to design a pair of degenerate primers to amplify part fragment of the phytase gene from the *Yersinia intermedia* chromosomal DNA by PCR.

<3-1> Obtaining a Part of Phytase Gene

Degenerate primers were designed based on the two conserved sequences and were synthesized by using a DNA synthesizer. The *Yersinia intermedia* chromosomal DNA was used as a template for PCR amplification. Except for degenerate primers and chromosomal DNA template, other reagent used for PCR amplification were purchase from TIANGEN BIOTECH CO., LTD. By optimizing of PCR parameters, we determined the PCR annealing temperature to be 50° C. and the PCR conditions were as follows: 1 cycle at 95° C. for 2 minutes, followed by 30 cycles at: 95° C. 30 seconds/annealing temperature for 30-40 seconds/72° C. for 1 minute, and a final extension of 5 minutes at 72° C., and PCR products were stored at 4° C. The amplification products were visualized by electrophoresis on agarose gel, and a series of bands amplified by the degenerate primers were observed. Using a suitable DNA ladder, the bands of the desired size (900 bp) could be chose. As a result, a DNA band approximate 900 bp was purified by TaKaRa Agarose Gel DNA Purification Kit, and the DNA purified was cloned into the PCR cloning vector pGEMTeasy (Promega), and then transformed into *E. coli* JM109. The transformed strains with the target DNA fragment were isolated, the plasmid containing the target DNA fragment was extracted, and the approximate 900 bp DNA was sequenced. As a result, a 901 bp DNA sequence was confirmed to be a partial phytase gene.

<3-2> Cloning of Phytase Gene

In order to obtain the whole sequence of the phytase gene, the upstream and downstream regions of the 901 bp sequence were cloned respectively by Thermal Asymmetric Interlaced PCR (Liu et al., 1995). Since TAIL-PCR is a powerful tool for the recovery of DNA fragments adjacent to known sequences, and is a very fast and cost-effective approach. Based on the known 901 bp fragment, the nested insertion-specific primers for TAIL PCR were designed, and named respectively as

```
usp1
                                        (SEQ ID NO: 8)
(5'-CTATTCCATCAAGGAATGCCTGCCCCG-3') (up special
primer),
usp2
                                        (SEQ ID NO: 9)
(5'-CGCGTTCGTTGATCAACATCGGCCtg-3'),
usp3
                                        (SEQ ID NO: 10)
(5'-GGGTTAAGTATCCTGCGGCG-3'),
dsp1
```

-continued

```
                                        (SEQ ID NO: 11)
(5'-GTTGCCTGGCATCGGTTAACGGGAG -3) (down special
primer),
dsp2
                                        (SEQ ID NO: 12)
(5'-CGCTCGTCATAAGGGCACACCGTTGC-3'),
and
dsp3
                                        (SEQ ID NO: 13)
(5'-ccgtctcattattgtttattgctgg-3').
```

The other terminal primers, arbitrary degenerate primers (AD primers, including AD6: 5'-CAWCGICNGAIASGAA-3', (SEQ ID NO: 14) AD9: 5'-WCAGNTGWTNGTNCTG-3') (SEQ ID NO: 15), were the key to TAIL PCR for successful amplification. Nested insertion-specific primers are used together with AD primers, which are designed to differ in their annealing temperatures. The amplification program of TAIL-PCR was substantially the same to Liu's (Liu et al., Thermal asymmetric interlaced PCR: automatable amplification and sequencing of insert end fragments from P1 and YAC clones for chromosome walking. Genomics. 1995 Feb. 10; 25(3):674-81)), which is incorporated herein for reference in its entirety. Alternating cycles of high and low annealing temperature yield specific products bordered by an insertion-specific primer on one side and an AD primer on the other. By agarose gel analysis of TAIL-PCR products, we had obtained approx 900 bp upstream DNA of the known sequence, and by optimizing of TAIL-PCR parameters, we also had obtained approx 650 bp downstream DNA of the known sequence. Respectively, the two bands of DNA was purified by TaKaRa Agarose Gel DNA Purification Kit, the DNA purified were cloned into the PCR cloning vector pGEMTeasy (Promega), and then transformed into *E. coli* JM109. The two bands of DNA were sequenced respectively.

All the three sequences were inputted in DNASTAR and assembled by sequence analysis program, by which an open reading frame was determined. The open reading frame of 1326 bp was composed of a signal sequence and an active protein.

<3-3> Analysis of a the Whole Sequence Obtained

The whole sequence obtained consists of 2354 bp, containing an open reading frame (1326 bp) (SEQ ID NO: 2), which was found by the ORF find program in Vector NTI. This ORF encode a signal peptide and an active protein. The most likely position of the cleavage site of signal peptide at the N-terminus, Ser23-Ala24, was determined using the Signal P program [http://www.cbs.dtu.dk/services/SignalP/] and multiple sequence alignment. This data on the localization of the N-terminus of the mature active protein is necessary to produce the active protein in heterologous systems. The molecular mass of the mature peptide was determined using PeptideMass [http://cn.expasy.org/tools/peptide-mass html]. The predicted mass of the peptide (45.5 kDa) was agreed with the SDS-PAGE value (about 45 kDa) (FIG. 1). And the theoretical pI value of this protein predicated by Vector NTI 7.0 is around 7.7.

Homology searches in GenBank were done using the BLAST server [http://www.ncbi.nlm.nih.gov/BLAST]. As a result, the amino acid sequence (SEQ ID NO: 3) of the ORF showed a low homology (54%) with the known phytase from *Obesumbacterium proteus*, and had a low homology (45%) with AppA from *E. coli*. Therefore, it was conformed that the ORF from *Yersinia intermedia* coded a novel phytase. The amino acid sequence of ORF from *Yersinia intermedia* was named AppA like other name of phytases. Although there is a high homology hit of a hypothetical sequence from *Yersinia* intermedia ATCC 29909, however, this hypothetical protein was derived from an annotated genomic sequence (NZ AALF01000052) by automated computational analysis without confirmation of the enzymatic activities or any information concerning the physical or chemical characteristics.

Example 4

Expression of AppA in *Pichia Pastoris*

<4-1> Construction of the Expressing Vectors
In order to isolate the coding region of mature protein, Primers

```
yermF:
                                    (SEQ ID NO: 16)
5'-GCGGAATTCGCCGCGCCGGTTGCCATA-3' (27 mer),
and yermR:
                                    (SEQ ID NO: 17)
5'-GTAGCGGCCGCTTAAATATGGCAAGCAGGTTC-3' (32 mer),
``` were synthesized. The coding region of mature protein was amplified using yermF-yermR. The amplification products were visualized by electrophoresis on agarose gel, and band of expected size was excised and DNA was extracted with TaKaRa Agarose Gel DNA Purification Kit. The DNA purified was inserted into pPIC9 (Invitrogen, San Diego, Calif.) at the EcoRI and NotI sites, as described by the manufacturer instruction. The constructs were transformed into JM109 cells which were plated on LB medium containing 100 μg amp/mL. The positive colony was sequenced, and was grown for preparation of DNA for yeast transformation.

<4-2> Yeast Transformation and Expression
*Pichia pastoris* strain GS115 (Invitrogen) were grown in YPD medium and prepared for transformation, according to the manufacturer instructions. 8 μg of plasmid DNA pPIC9 was linearized using DraI, and then transformed into *Pichia* by electroporation. The cells transformed were plated in RDB agar medium to screen integration of HIS4 gene into the host chromosomal DNA. The transformants containing transformed HIS4 gene would grow in the RDB plates. After 3 days, the transformants were incubated in minimal media with glycerol (BMGY medium) for 48 h, and then the cells were spun down (2500 g, 5 min) and suspended in 0.5% methanol medium (BMMY) to induce the phytase gene expression.

<4-3> Measurement of Phytase Activity of Transformants
A total of 72 transformants were analyzed for phytase activity by ferrous sulfate-molybdenum blue method. 950 μl of substrate solution (4 mM sodium phytase in 0.25M sodium acetate buffer, pH5.0) was added to 50 μl diluted enzyme solution, which was reacted at 37° C. for 30 minutes. Then, 1 mL of 10% TCA (trichloroacetic acid) solution was added to stop the reaction. As a control, TCA solution was added into the enzyme solution to inactivate the enzyme and then substrate solution was added. After the reaction has terminated, 2 mL of reagent C (0.576M acid sulfate, 1% ammonium molybdate, 7.32% Ferrous sulfate.7$H_2O$) was added, and left for 10 minutes. The intensity of the blue color was measured at 700 nm, and activities in enzyme solution and in a control were measured. 1 unit of phytase activity was determined to be the enzyme amount releasing 1 μmol of phosphate for 1 minute. Two days after methanol induction, 11 transformants out of 72 produced phytase activity from 48 to 270 U/mL of medium. Obviously, the ORF obtained above, was a novel gene, which encoded a polypeptide with phytase activity. The polypeptide with phytase activity, which encoded by mature region of OFR, was named r-AppA.

Example 5

Purification of r-AppA Expressed in *Pichia Pastoris*

In order to purify the phytase produced by *Pichia pastoris*, the transformant with 270 U/mL of medium was cultured under the optimal culture and induction conditions. Two days after methanol induction, the phtase activity was measured with the same method as used in the above example 4, and the enzyme activity produced was 389 unit/ml in supernatant. The supernatant was obtained by centrifugation with 12000 g for 10 minutes, and the precipitated cells were discarded.

Ammonium sulfate powder was added into the supernatant until 80% saturation, followed by centrifugation at 12000 g for 10 minutes to recover the precipitate. Sodium acetate buffer solution (0.1M, pH5.0) was added to the precipitate to dissolve it, followed by centrifugation at 12000 g for 10 minutes. Then, the supernatant was obtained, and dialysis performed by using the same buffer solution. Subsequently the resulting dialyzate was further concentrated in a Filtron ultrafiltration unit with 10 kDa cutoff filters. Finally, phytase was purified though Sephacryl S-200 with the same buffer solution that was used in the dialysis. Thereby the separated phytase was finally purified.

Example 6

Characteristics of r-AppA Expressed in *Pichia Pastoris*

Figure 1:
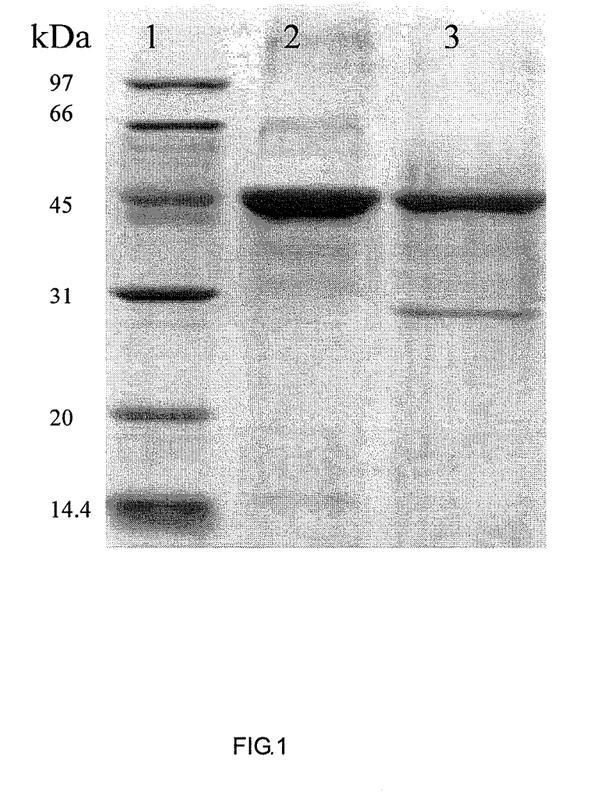
FIG. 1 shows the result of SDS-PAGE with phytase purified and the phytase deglycosylated.

<6-1> Determination of Molecular Weight and Deglycosylation of r-AppA
The molecular weight of purified r-AppA was measured by SDS-PAGE electrophoresis. FIG. 1 lane 1: was marker protein whose size was known, lane 2: was the purified r-AppA, lane 3: was deglycosylated r-AppA. According to the measurement, r-AppA purified through Sephacryl S-200 was confirmed to have molecular weight of about 45 kDa. The sequence of r-AppA was predicted by using the NetNglyc server program [http://www.cbs.dtu.dk/services/NetNGlyc]. There was no potential N-glycosylation sites (Asn-Xaa-Ser/Thr) existed in this phytase sequence. The same result was observed from FIG. 1. Because the purified r-AppA, after treatment with endoglycosidase H had the same molecular weight (about 45 kDa) as the r-AppA without treatment with endoglycosidase H.

Figure 2:
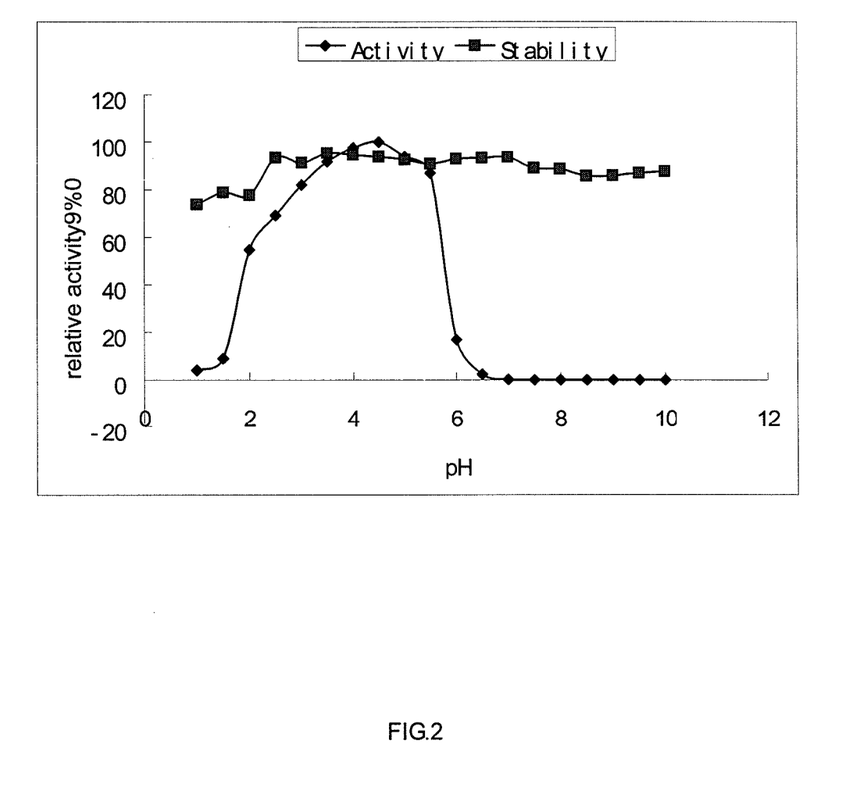
FIG. 2 shows optimum pH values and pH stabilities for novel phytases. The activity at each pH value is exhibited as a relative activity (%) to the activity as 100%, which has been determined under pH conditions conferring a maximum activity.

<6-2> Enzyme Activity of r-AppA According to Temperature and pH
The r-AppA purified through Sephacryl S-200 was investigated an enzyme activity of phytase, according to temperature and pH. The effect of pH on phytase activity was determined using the following buffer solutions: glycine-HCl, pH 1.5-3.5; Na acetate-acetic acid, pH 3.5-6.0; Tris-HCl, pH 6.0-8.5, and glycine-NaOH, pH 8.5-10. All buffers used for dilution contained 0.05% BSA and 0.05% Triton. As is shown in FIG. 2, the enzyme activity varied with pH. The highest activity was observed at pH 4.5. 70% of the enzyme activity was still maintained at pH 2.5, and 65% of the enzyme activity was still maintained at pH 5.5. Obviously, the r-AppA had a strong enzyme activity in a favourable pH range from pH 2 to pH 6, comparing to other conventional phytases. FIG. 2 shows the enzyme activity was very stably and over 85% activity remained, when the enzyme maintained at 37° C., at pH 2.5-10 for 2 hours. And over 70% activity still remained at pH 1.0-2.0.

Figure 3A:
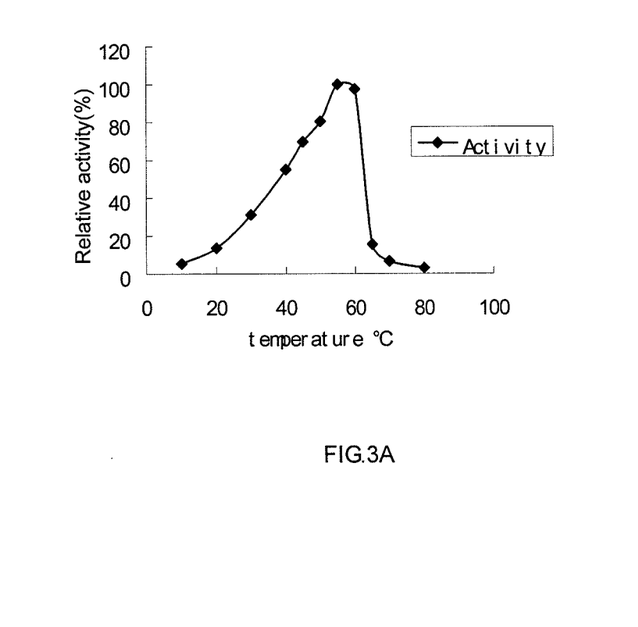
FIG. 3A shows optimum temperatures for novel phytases. The activity at each temperature is exhibited as a relative activity (%) to the activity as 100%, which has been determined under conditions of temperature conferring a maximum activity.
Figure 3B:
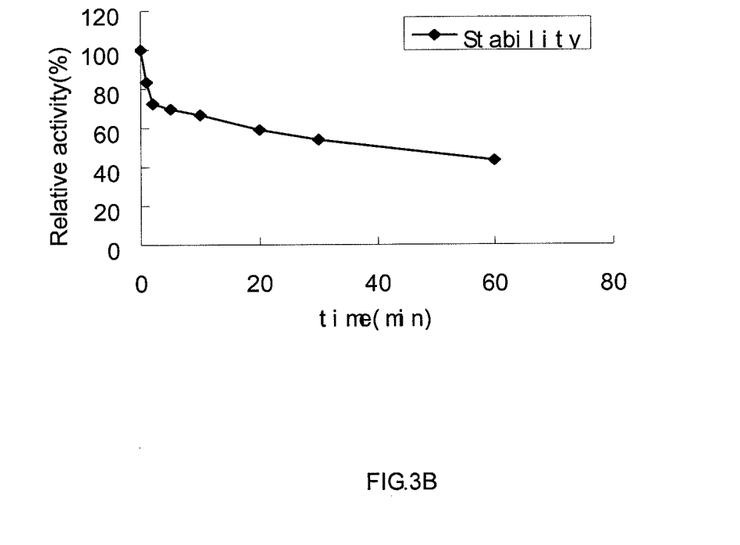
FIG. 3B shows heat stability for novel phytases at 80° C.

As is shown in FIG. 3A, the enzyme activity varied with temperature. The temperature optima were determined at the pH optimum (pH 4.5) ranging the temperature values from 20 to 80° C. The highest activity was observed at 55° C. As is shown in FIG. 3B, when the enzyme was left at 80° C. for 10 minutes, over 50% of the activity was remained, and 40% of the activity was remained, at 80° C. for 1 hour. Compared to AppA from *E. coli*, which was widely used in feed industry as a feed additive, the r-AppA are higher stability at higher temperatures.

According to the temperature and pH test with r-AppA, and in comparison to other conventional phytases, phytase of the present invention was believed to be very suitable for use as a feed additive for monogastric animals. As the offered phytase has widely pH stability and high temperature stability, compared to commonly used phytases, r-AppA has a great potential commercial application value.

<6-3> Enzyme Activity of r-AppA According to Metal Ions and Inhibitors

The effect of metal ions on r-AppA activity was investigated at the pH optimum (pH 4.5). As is shown in Table 4, among various metal ions, the enzyme activity of r-AppA were weakly inhibited by many metal ions under the concentration of 1 mM, and were obviously inhibited by $Fe^{2+}$, $Zn^{2+}$ and $Cu^{2+}$. And the enzyme activity was weakly enhanced by $Mn^{2+}$. As for inhibitors, the enzyme activity was strongly affected by SDS, and the enzyme activity was almost lost. However, the enzyme activity was not significantly changed with EDTA, and the enzyme activity was the same as the control.

TABLE 4

Enzyme activity of r-AppA according to metal ions and inhibitors

| | |
|---|---|
| Na | 95 |
| K | 99 |
| Ca | 98 |
| Li | 95 |
| Co | 93 |
| Cr | 88 |
| Ni | 98 |
| Cu | 61 |
| Mg | 94 |
| Fe | 47 |
| Mn | 104 |
| Zn | 44 |
| EDTA | 101 |
| SDS | 9 |
| Ag | 84 |
| control | 100 |

<6-4> Effect of Proteases on the Enzyme Activity of r-AppA

Figure 4:
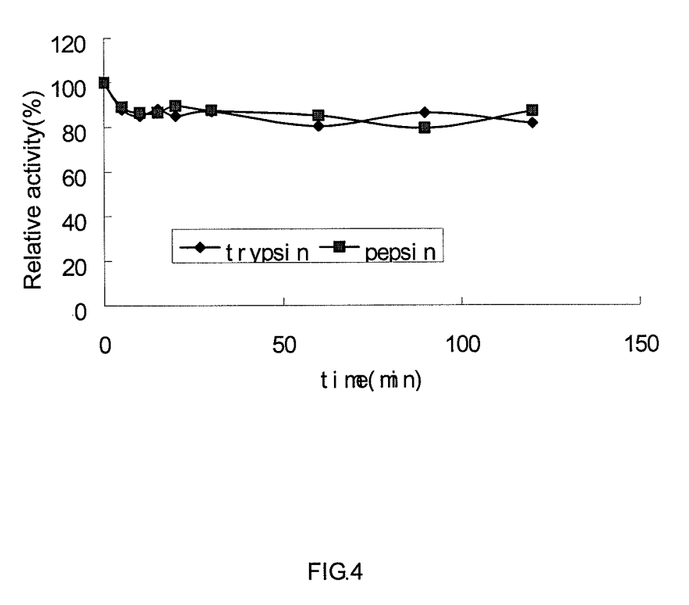
FIG. 4 shows proteases stability for novel phytase.

To determine the protease resistance, the purified phytase (0.025 mg/ml) was incubated with 0.1 mg/ml of pepsin and trypsin at 37° C. And then, sample incubated was collected respectively at 5 min, 10 min, 20 min, 30 min, 1 h, and 2 hs. As is shown in the FIG. 4, phytase activity was not significantly changed with either pepsin or trypsin. This phytase thus showed higher protease resistance than any other phytase previously reported. The result suggested that phytase could promote coefficient of the enzyme inside monogastric animals owing to its resistance against pepsin and trypsin existed in stomach or intestines.

<6-5> Determination of Specific Activity

In order to determinate the specific activity, the concentration of the r-AppA purified through Sephacryl S-200 was determined by the Lowry method, and the enzyme activity of the r-AppA purified was determined by ferrous sulfate-molybdenum blue method at pH 4.5. As a result, the specific activity of r-AppA purified was 3960±248 U/mg, which is the highest specific activity, comparing to other phytases recorded previously.

INDUSTRIAL APPLICABILITY

As described in detail in the above paragraphs, the invention produces a novel phytase has several advantages: high specific activity, favourable pH-optimum, high stability at higher temperatures, resistance against proteases, easily produce by fermentation. All these advantages mean the phytase is more useful than any other conventional phytases as a feed additive. Firstly, high specific activity means that the phytase producing the same can be effectively used as a feed additive for monogastric animals and for the recovery of specific degradation product of phytic acid at low price; Secondly, favourable pH-optimum means that the phytase has a very high activity to degrade phytic acid in stomach or intestines; Thirdly, high stability at higher temperatures means that the phytase resistance against at high temperature during feed pelleting process; Fourthly, resistance against proteases means that the phytase maintains high enzyme activity without being decomposed in intestines or stomach; Finally, easily produce by fermentation it means that the phytase could be obtained easily, and could widely use in feed industry. Based on the above excellent characteristic, any one of ordinary skill in the art knows that the inventive protein products will play an important role in feed industry as a feed additive. This new phytase isolated from *Yersinia intermedia* has overcome the disadvantages in the prior art, thus has a great commercial potential.

REFERENCE

E Graf, K L Empson and J W Eaton. Phytic acid. A natural antioxidant. J. Biol. Chem., Vol. 262, Issue 24, 11647-11650, August, 1987

Cromwell G L, Stahly T S, Coffey R D, Monegue H J, Randolph J H. Efficacy of phytase in improving the bioavailability of phosphorus in soybean meal and corn-soybean meal diets for pigs. J Anim Sci. 1993 July; 71(7):1831-40.

Kornegay E T, Qian H. Replacement of inorganic phosphorus by microbial phytase for young pigs fed on a maize-soya-bean-meal diet. Br J Nutr. 1996 October; 76(4):563-78.

Greiner R, Haller E, Konietzny U, Jany K D. Purification and characterization of a phytase from *Klebsiella terrigena*. Arch Biochem Biophys. 1997 May 15; 341(2):201-6.

Kim Y.-O.; Kim H.-K.; Bae K.-S.; Yu J.-H.; Oh T.-K. Purification and properties of a thermostable phytase from *Bacillus* sp. DS11. Enzyme Microb Technol, 1998 January, 22(1), 2-7

Kim H W, Kim Y O, Lee J H, Kim K K, Kim Y J. Isolation and characterization of a phytase with improved properties from *Citrobacter braakii*. Biotechnol Lett. 2003 August; 25(15):1231-4.

Zinin N V, Serkina A V, Gelfand M S, Shevelev A B, Sineoky S P. Gene cloning, expression and characterization of novel phytase from *Obesumbacterium proteus*. FEMS Microbiol Lett. 2004 Jul. 15; 236(2):283-90.

Chen et al, Improving thermostability of *Aspergillus niger* phytase by elongation mutation. Chinese Journal of Biotechnology, November 2005; 21(6): 983-987.

Lei X G. Site-directed mutagenesis of *Escherichia coli* phytase. U.S. Pat. No. 6,841,370. 2005

Liu Y G, Whittier R F. Thermal asymmetric interlaced PCR: automatable amplification and sequencing of insert end fragments from P1 and YAC clones for chromosome walking. Genomics. 1995 Feb. 10; 25(3):674-81.

H Y Luo, B Yao, T Z Yuan, Y R Wang, X Y Shi, N F Wu, Y L Fan. Overexpression of *Escherichia coli* phytase with high specific activity. Sheng Wu Gong Cheng Xue Bao. 2004 January; 20(1):78-84.

O. Simon, F. Igbasan. In vitro properties of phytases from various microbial origins. International Journal of Food Science and Technology 2002, 37, 813-822

A. Casey, G. Walsh. Purification and characterization of extracellular phytase from *Aspergillus niger* ATCC 9142. Bioresour Technol. 2003 January; 86(2):183-8.

What is claimed is:

1. An isolated phytase protein with improved thermostability, which is selected from:
   a) a polypeptide comprising an amino acid sequence that is at least 95% identical to the amino acid sequence of SEQ ID NO. 3; or
   b) a polypeptide encoded by a polynucleotide that is at least 90% identical to the polynucleotide of SEQ ID NO: 2; wherein said phytase has over 40% of the activity left when kept at 80° C. for 1 hour.

2. The protein according to claim 1, which is selected from:
   a) a polypeptide comprising the amino acid sequence of SEQ ID NO.3; or
   b) a polypeptide encoded by the polynucleotide sequence of SEQ ID NO:2.

3. The protein according to claim 2, which is from A Yersinia intermedia H-27 strain with the accession No. CGMCC 1702.

* * * * *

SEQUENCE LISTING

<160> NUMBER OF SEQ ID NOS: 17

<210> SEQ ID NO 1
<211> LENGTH: 1440
<212> TYPE: DNA
<213> ORGANISM: Yersinia intermedia

<400> SEQUENCE: 1

```
ccgtccggat tgtgtacgtt cagctcgccg tcgcccttca tcaaatgatg aaacggccgc      60
tcgccgcctg cccactcatt acagaccctt tgacggacta cctcccccta ttgatgacct     120
ttgccatcga ttatggcgta ctggagcgtt ctcgtttcac ccctggaag cccggagtgc      180 ggtagcctac acgggtctac cctaatcgat catccacccc attaccgagt ggatccgctg     240
ctagggatcg accagactct cctactggtc ggtgtgacct tgactctgtg ccaggtctga     300
ggatgccctc cgtcgtcacc ccttataacg tgttacccgc gttcggacta cgtcggtacg     360
gcgcacacac ttcttccgga agcccaacat ttcgtgaaag tcgctcctcc ttccgtcagc     420
acaattatcg tgctaactaa ctgcaatgag cgtcttcttc gtggccgatt gaggcacggt     480
cgtcggcgcc attatgcctc ccacgttcgc aattagcctt aatgacccgc atttcgcgtg     540
cgtccgccaa acaattcagt ctacacttta ggggcgcgaa ttgcacccct gacgtaaact     600
ttgaccgttc gatctcagaa catctccccc catcttaagg tccacatcgc cactttacgc     660
atctctagac ctccttatgg ccaccgcttc cgccggggga cctgtttctg actgcgagtc     720
cacgctttcg caccctcgt ttgtcctaat ctatgggacc atcaggtgcg acatttgcta     780
cagctgaacc tccaacacgg gaactccgca ccgaaggcct cgattgcgca attcagctgg     840
cggacccctc atgccggcgt tccaattttg agtttactta actgccccg ggcgtgttcg      900 ccacctcgta caccaaatta agctacgttg cgcttcttgg aatggatgag aactgtaggt     960
gccttaaatc gtctctacga agtcacggaa gcccttggca ctctgtccac gacgtaccga    1020
cagcagtcga gcacaacact ttacaaccca attcagggcg ttgctcgcgt tgggaatagg    1080
aaacaacggt cgtgcattac cacccttgag ttccctctga cggccactgt ttggcctcct    1140
tccaccccta ctgcagttca gtagtaccgg gaatgctcat cccgatgtgt gcacgatgtt    1200
acgcgtctat gtttcacttc gcttgagcgc tctcgttcgc ctggtgtatt tcagacagca    1260
tcaggcctaa cctcagacgt tgagctgagg tacttcagcc ttagcgatca ttagcatcta    1320
gtcttacgat gccacttatg caagggcccg gaacatgtgt ggcgggcagt gtggtaccct    1380
cacccaacgt tttcttcatc catcgaattg gaagccctcc cgcgaatggt gaaacactaa    1440
```

<210> SEQ ID NO 2
<211> LENGTH: 1326
<212> TYPE: DNA
<213> ORGANISM: Yersinia intermedia
<220> FEATURE:
<221> NAME/K

```
atc tcg tta tta tcg ttg cac aat gcg caa ttt gat tta atg gca aaa         864
Ile Ser Leu Leu Ser Leu His Asn Ala Gln Phe Asp Leu Met Ala Lys
        275                 280                 285 aca cct tat atc gct cgt cat aag ggc aca ccg ttg ctg caa cag atc         912
Thr Pro Tyr Ile Ala Arg His Lys Gly Thr Pro Leu Leu Gln Gln Ile
    290                 295                 300 gag act gcc ctc gtc ctt cag cgt gat gct cag ggg caa aca ttg cca         960
Glu Thr Ala Leu Val Leu Gln Arg Asp Ala Gln Gly Gln Thr Leu Pro
305                 310                 315                 320 tta tca cct caa acc aaa att ctg ttc ctc ggg gga cat gat aca aac        1008
Leu Ser Pro Gln Thr Lys Ile Leu Phe Leu Gly Gly His Asp Thr Asn
                325                 330                 335 atc gcc aat att gct gga atg ttg ggg gct aac tgg caa tta cca cag        1056
Ile Ala Asn Ile Ala Gly Met Leu Gly Ala Asn Trp Gln Leu Pro Gln
        340                 345                 350 cag ccc gat aat acc cca cct ggg ggg gga ttg gtc ttc gag cta tgg        1104
Gln Pro Asp Asn Thr Pro Pro Gly Gly Gly Leu Val Phe Glu Leu Trp
    355                 360                 365 caa aac cca gat aat cat caa cgt tat gtc gcg gtg aaa atg ttc tat        1152
Gln Asn Pro Asp Asn His Gln Arg Tyr Val Ala Val Lys Met Phe Tyr
370                 375                 380 caa aca atg ggc caa ttg cga aat gct gag aaa cta gac ctg aaa aac        1200
Gln Thr Met Gly Gln Leu Arg Asn Ala Glu Lys Leu Asp Leu Lys Asn
385                 390                 395                 400 aat ccg gct ggt agg gtc cct gtt gca ata gac ggt tgt gaa aat agt        1248
Asn Pro Ala Gly Arg Val Pro Val Ala Ile Asp Gly Cys Glu Asn Ser
                405                 410                 415 ggt gat gac aaa ctt tgt cag ctt gat acc ttc caa aag aaa gta gct        1296
Gly Asp Asp Lys Leu Cys Gln Leu Asp Thr Phe Gln Lys Lys Val Ala
        420                 425                 430 cag gcg att gaa cct gct tgc cat att taa                                1326
Gln Ala Ile Glu Pro Ala Cys His Ile
    435                 440
```

<210> SEQ ID NO 3
<211> LENGTH: 441
<212> TYPE: PRT
<213> ORGANISM: Yersinia intermedia

<400> SEQUENCE: 3

```
Met Thr Ile Thr Val Asp Ser Leu Arg Leu Ser Val Leu Thr Leu Ile
1               5                   10                  15

Leu Asn Ser Tyr Ala Ile Ser Ala Ala Pro Val Ala Ile Gln Pro Thr
            20                  25                  30

Gly Tyr Thr Leu Glu Arg Val Val Ile Leu Ser Arg His Gly Val Arg
        35                  40                  45

Ser Pro Thr Lys Gln Thr Gln Leu Met Asn Asp Val Thr Pro Asp Thr
    50                  55                  60

Trp Pro Gln Trp Pro Val Ala Ala Gly Tyr Leu Thr Pro Arg Gly Ala
65                  70                  75                  80

Gln Leu Val Thr Leu Met Gly Gly Phe Tyr Gly Asp Tyr Phe Arg Ser
                85                  90                  95

Gln Gly Leu Leu Ala Ala Gly Cys Pro Thr Asp Ala Val Ile Tyr Ala
            100                 105                 110

Gln Ala Asp Val Asp Gln Arg Thr Arg Leu Thr Gly Gln Ala Phe Leu
        115                 120                 125

Asp Gly Ile Ala Pro Gly Cys Gly Leu Lys Val His Tyr Gln Ala Asp
    130                 135                 140

Leu Lys Lys Val Asp Pro Leu Phe His Pro Val Asp Ala Gly Val Cys
```

-continued

```
                145                 150                 155                 160
Lys Leu Asp Ser Thr Gln Thr His Lys Ala Val Glu Glu Arg Leu Gly
                    165                 170                 175
Gly Pro Leu Ser Glu Leu Ser Lys Arg Tyr Ala Lys Pro Phe Ala Gln
                180                 185                 190
Met Gly Glu Ile Leu Asn Phe Ala Ala Ser Pro Tyr Cys Lys Ser Leu
            195                 200                 205
Gln Gln Gln Gly Lys Thr Cys Asp Phe Ala Asn Phe Ala Ala Asn Lys
        210                 215                 220
Ile Thr Val Asn Lys Pro Gly Thr Lys Val Ser Leu Ser Gly Pro Leu
225                 230                 235                 240
Ala Leu Ser Ser Thr Leu Gly Glu Ile Phe Leu Leu Gln Asn Ser Gln
                    245                 250                 255
Ala Met Pro Asp Val Ala Trp His Arg Leu Thr Gly Glu Asp Asn Trp
                260                 265                 270
Ile Ser Leu Leu Ser Leu His Asn Ala Gln Phe Asp Leu Met Ala Lys
            275                 280                 285
Thr Pro Tyr Ile Ala Arg His Lys Gly Thr Pro Leu Leu Gln Gln Ile
        290                 295                 300
Glu Thr Ala Leu Val Leu Gln Arg Asp Ala Gln Gly Gln Thr Leu Pro
305                 310                 315                 320
Leu Ser Pro Gln Thr Lys Ile Leu Phe Leu Gly Gly His Asp Thr Asn
                    325                 330                 335
Ile Ala Asn Ile Ala Gly Met Leu Gly Ala Asn Trp Gln Leu Pro Gln
                340                 345                 350
Gln Pro Asp Asn Thr Pro Pro Gly Gly Gly Leu Val Phe Glu Leu Trp
            355                 360                 365
Gln Asn Pro Asp Asn His Gln Arg Tyr Val Ala Val Lys Met Phe Tyr
        370                 375                 380
Gln Thr Met Gly Gln Leu Arg Asn Ala Glu Lys Leu Asp Leu Lys Asn
385                 390                 395                 400
Asn Pro Ala Gly Arg Val Pro Val Ala Ile Asp Gly Cys Glu Asn Ser
                    405                 410                 415
Gly Asp Asp Lys Leu Cys Gln Leu Asp Thr Phe Gln Lys Lys Val Ala
                420                 425                 430
Gln Ala Ile Glu Pro Ala Cys His Ile
            435                 440

<210> SEQ ID NO 4
<211> LENGTH: 20
<212> TYPE: DNA
<213> ORGANISM: Artificial Sequence
<220> FEATURE:
<223> OTHER INFORMATION: Forward degenerate primer

<400> SEQUENCE: 4
gtkstkawwk tsagycgcca                                                   20

<210> SEQ ID NO 5
<211> LENGTH: 20
<212> TYPE: DNA
<213> ORGANISM: Artificial Sequence
<220> FEATURE:
<223> OTHER INFORMATION: Reverse degenerate primer

<400> SEQUENCE: 5
twkgcmakrt trgtatcrtg                                                   20
```

<210> SEQ ID NO 6
<211> LENGTH: 7
<212> TYPE: PRT
<213> ORGANISM: Artificial Sequence
<220> FEATURE:
<223> OTHER INFORMATION: Conserved sequence
<220> FEATURE:
<221> NAME/KEY: MISC_FEATURE
<222> LOCATION: (4)..(4)
<223> OTHER INFORMATION: Xaa corresponds to X in application
<220> FEATURE:
<221> NAME/KEY: MISC_FEATURE
<222> LOCATION: (6)..(6)
<223> OTHER INFORMATION: Xaa corresponds to X in application

<400> SEQUENCE: 6

Thr His Gly Xaa Arg Xaa Phe
1               5

<210> SEQ ID NO 7
<211> LENGTH: 7
<212> TYPE: PRT
<213> ORGANISM: Artificial Sequence
<220> FEATURE:
<223> OTHER INFORMATION: Conserved sequence
<220> FEATURE:
<221> NAME/KEY: MISC_FEATURE
<222> LOCATION: (4)..(4)
<223> OTHER INFORMATION: Xaa corresponds to X in application
<220> FEATURE:
<221> NAME/KEY: MISC_FEATURE
<222> LOCATION: (6)..(6)
<223> OTHER INFORMATION: Xaa corresponds to X in application

<400> SEQUENCE: 7

Arg His Gly Xaa Arg Xaa Phe
1               5

<210> SEQ ID NO 8
<211> LENGTH: 27
<212> TYPE: DNA
<213> ORGANISM: Artificial Sequence
<220> FEATURE:
<223> OTHER INFORMATION: Up special primer

<400> SEQUENCE: 8
ctattccatc aaggaatgcc tgccccg                                       27

<210> SEQ ID NO 9
<211> LENGTH: 26
<212> TYPE: DNA
<213> ORGANISM: Artificial Sequence
<220> FEATURE:
<223> OTHER INFORMATION: Up special primer

<400> SEQUENCE: 9
cgcgttcgtt gatcaacatc ggcctg                                        26

<210> SEQ ID NO 10
<211> LENGTH: 20
<212> TYPE: DNA
<213> ORGANISM: Artificial Sequence
<220> FEATURE:
<223> OTHER INFORMATION: Up special primer

<400> SEQUENCE: 10
gggttaagta tcctgcggcg                                               20

<210> SEQ ID NO 11

```
<211> LENGTH: 25
<212> TYPE: DNA
<213> ORGANISM: Artificial Sequence
<220> FEATURE:
<223> OTHER INFORMATION: Down special primer

<400> SEQUENCE: 11
gttgcctggc atcggttaac gggag                                              25

<210> SEQ ID NO 12
<211> LENGTH: 26
<212> TYPE: DNA
<213> ORGANISM: Artificial Sequence
<220> FEATURE:
<223> OTHER INFORMATION: Down special primer

<400> SEQUENCE: 12
cgctcgtcat aagggcacac cgttgc                                             26

<210> SEQ ID NO 13
<211> LENGTH: 25
<212> TYPE: DNA
<213> ORGANISM: Artificial Sequence
<220> FEATURE:
<223> OTHER INFORMATION: Down special primer

<400> SEQUENCE: 13
ccgtctcatt attgtttatt gctgg                                              25

<210> SEQ ID NO 14
<211> LENGTH: 16
<212> TYPE: DNA
<213> ORGANISM: Artificial Sequence
<220> FEATURE:
<223> OTHER INFORMATION: Arbitrary degenerate primer
<220> FEATURE:
<221> NAME/KEY: misc_feature
<222> LOCATION: (6)..(11)
<223> OTHER INFORMATION: For residues 6 and 11, n is inosine and for
      residue 8, n is a, c, g or t

<400> SEQUENCE: 14
cawcgncnga nasgaa                                                        16

<210> SEQ ID NO 15
<211> LENGTH: 16
<212> TYPE: DNA
<213> ORGANISM: Artificial Sequence
<220> FEATURE:
<223> OTHER INFORMATION: Arbitrary degenerate primer
<220> FEATURE:
<221> NAME/KEY: misc_feature
<222> LOCATION: (5)..(13)
<223> OTHER INFORMATION: For residues 5, 10 and 13, n is a, c, g or t

<400> SEQUENCE: 15
wcagntgwtn gtnctg                                                        16

<210> SEQ ID NO 16
<211> LENGTH: 27
<212> TYPE: DNA
<213> ORGANISM: Artificial Sequence
<220> FEATURE:
<223> OTHER INFORMATION: Primer

<400> SEQUENCE: 16
gcggaattcg ccgcgccggt tgccata                                            27
```

```
<210> SEQ ID NO 17
<211> LENGTH: 32
<212> TYPE: DNA
<213> ORGANISM: Artificial Sequence
<220> FEATURE:
<223> OTHER INFORMATION: Primer

<400> SEQUENCE: 17
gtagcggccg cttaaatatg gcaagcaggt tc                              32
```